(12) United States Patent
Kurada et al.

(10) Patent No.: US 9,563,943 B2
(45) Date of Patent: *Feb. 7, 2017

(54) BASED SAMPLING AND BINNING FOR YIELD CRITICAL DEFECTS

(71) Applicant: KLA-Tencor Corporation, Milpitas, CA (US)

(72) Inventors: Satya Kurada, Fremont, CA (US); Raghav Babulnath, San Jose, CA (US); Kwok Ng, Milpitas, CA (US); Lisheng Gao, Morgan Hill, CA (US)

(73) Assignee: KLA-Tencor Corp., Milpitas, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/092,510

(22) Filed: Apr. 6, 2016

(65) Prior Publication Data

US 2016/0225138 A1 Aug. 4, 2016

Related U.S. Application Data

(63) Continuation of application No. 14/251,415, filed on Apr. 11, 2014, now Pat. No. 9,310,320.

(Continued)

(51) Int. Cl.
*G06K 9/00* (2006.01)
*G06T 7/00* (2006.01)
*G01N 21/956* (2006.01)
*G01N 21/95* (2006.01)

(52) U.S. Cl.
CPC ......... *G06T 7/0006* (2013.01); *G01N 21/9501* (2013.01); *G01N 21/956* (2013.01);

(Continued)

(58) Field of Classification Search
CPC ............... G06T 2207/30148; G06T 7/0006; G06T 2207/10061; G06T 7/001; G06T 2200/24; G06T 7/0004; G01N 21/9501; G01N 2021/95676; G01N 21/95607; G01N 2021/8825; G03F 1/84; G03F 7/7065; H01L 22/20; H01L 22/12; G06F 17/5081; G06K 9/6282; G06K 9/00; H01J 2237/2817

(Continued)

(56) References Cited

U.S. PATENT DOCUMENTS 6,336,082 B1 * 1/2002 Nguyen ............... G06K 9/6255
340/658
7,558,419 B1 * 7/2009 Ye ............................. G03F 1/84
382/144

(Continued)

*Primary Examiner* — Vu Le
*Assistant Examiner* — Aklilu Woldemariam
(74) *Attorney, Agent, or Firm* — Ann Marie Mewherter

(57) ABSTRACT

Methods and systems for design based sampling and binning for yield critical defects are provided. One method includes aligning each image patch in each inspection image frame generated for a wafer by an optical subsystem of an inspection system to design information for the wafer. The method also includes deriving multiple layer design attributes at locations of defects detected in the image patches. In addition, the method includes building a decision tree with the multiple layer design attributes. The decision tree is used to separate the defects into bins with different yield impacts on a device being formed on the wafer. The method also includes binning the defects with the decision tree.

19 Claims, 1 Drawing Sheet

Related U.S. Application Data

(60) Provisional application No. 61/811,910, filed on Apr. 15, 2013.

(52) U.S. Cl.
CPC ....... G01N 21/95607 (2013.01); G06T 7/001 (2013.01); G06T 7/0008 (2013.01); *G01N 2021/95676* (2013.01); *G01N 2201/068* (2013.01); *G01N 2201/06113* (2013.01); *G01N 2201/10* (2013.01); *G01N 2201/12* (2013.01); *G06K 9/00* (2013.01); *G06T 2207/30148* (2013.01)

(58) Field of Classification Search
USPC .... 382/144, 145, 149, 264, 232; 702/56, 81, 702/82, 179, 180, 181, 182, 183
See application file for complete search history.

(56) References Cited

U.S. PATENT DOCUMENTS

| | | | |
|---|---|---|---|
| 2006/0265145 A1* | 11/2006 | Huet | G01R 31/2846 702/35 |
| 2007/0156379 A1* | 7/2007 | Kulkarni | H01L 21/67005 703/14 |
| 2007/0230770 A1* | 10/2007 | Kulkarni | G06F 17/5045 382/149 |
| 2007/0288219 A1* | 12/2007 | Zafar | G03F 1/84 703/14 |
| 2008/0167829 A1* | 7/2008 | Park | G01N 21/8851 702/81 |
| 2008/0250384 A1* | 10/2008 | Duffy | G03F 7/7065 716/55 |
| 2010/0188657 A1* | 7/2010 | Chen | H01L 22/12 356/237.5 |
| 2011/0320149 A1* | 12/2011 | Lee | G01N 21/9501 702/83 |
| 2012/0229618 A1* | 9/2012 | Urano | G01N 21/9501 348/92 |
| 2013/0064442 A1* | 3/2013 | Chang | G06T 7/001 382/149 |
| 2013/0129189 A1* | 5/2013 | Wu | G06T 7/001 382/151 |
| 2013/0236084 A1* | 9/2013 | Li | G06T 7/001 382/144 |

* cited by examiner

BASED SAMPLING AND BINNING FOR YIELD CRITICAL DEFECTS

BACKGROUND OF THE INVENTION

1. Field of the Invention

This invention generally relates to design based sampling and binning for yield critical defects.

2. Description of the Related Art

The following description and examples are not admitted to be prior art by virtue of their inclusion in this section.

An integrated circuit (IC) design may be developed using a method or system such as electronic design automation (EDA), computer aided design (CAD), and other IC design software. Such methods and systems may be used to generate the circuit pattern database from the IC design. The circuit pattern database includes data representing a plurality of layouts for various layers of the IC. Data in the circuit pattern database may be used to determine layouts for a plurality of reticles. A layout of a reticle generally includes a plurality of polygons that define features in a pattern on the reticle. Each reticle is used to fabricate one of the various layers of the IC. The layers of the IC may include, for example, a junction pattern in a semiconductor substrate, a gate dielectric pattern, a gate electrode pattern, a contact pattern in an interlevel dielectric, and an interconnect pattern on a metallization layer.

The term "design data" as used herein generally refers to the physical design (layout) of an IC and data derived from the physical design through complex simulation or simple geometric and Boolean operations.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail.

As design rules shrink, however, semiconductor manufacturing processes may be operating closer to the limitations on the performance capability of the processes. In addition, smaller defects can have an impact on the electrical parameters of the device as the design rules shrink, which drives more sensitive inspections. Therefore, as design rules shrink, the population of potentially yield relevant defects detected by inspection grows dramatically, and the population of nuisance defects detected by inspection also increases dramatically. Therefore, more and more defects may be detected on the wafers, and correcting the processes to eliminate of the defects may be difficult and expensive.

In trying to maximize the sensitivity of the inspection system to capture subtle spatially systematic "design-for-manufacturability" (DFM) defects resulting from design and process interdependencies, the system may be overwhelmed by millions of events in non-critical areas such as CMP fill regions. Detecting such nuisance defects is disadvantageous for a number of reasons. For example, these nuisance events need to be filtered out of the inspection results by post-processing of the inspection data. In addition, nuisance event detection limits the ultimate achievable sensitivity of the inspection system for DFM applications. A high rate of nuisance defect data may also overload the run time data processing capacity of the inspection system thereby reducing throughput and/or causing the loss of data.

Accordingly, it would be advantageous to develop methods and/or systems for wafer inspection-related applications that do not have one or more of the disadvantages described above.

SUMMARY OF THE INVENTION

The following description of various embodiments is not to be construed in any way as limiting the subject matter of the appended claims.

One embodiment relates to a method for wafer inspection. The method includes scanning a wafer with an inspection system thereby generating image patches in inspection image frames for the wafer. The scanning step is performed with an optical subsystem of the inspection system. The method also includes aligning each of the image patches in each of the inspection image frames to design information for the wafer. In addition, the method includes detecting defects in the image patches. The method further includes deriving multiple layer design attributes at locations of the defects from the image patches corresponding to the locations of the defects. The method also includes building a decision tree with the multiple layer design attributes. The decision tree is used to separate the defects into bins with different yield impacts on a device being formed on the wafer. The method further includes binning the defects with the decision tree. The aligning, detecting, deriving, building, and binning steps are performed with one or more computer subsystems of the inspection system.

The method described above may be performed as described further herein. In addition, the method described above may include any other step(s) of any other method(s) described herein. Furthermore, the method described above may be performed by any of the systems described herein.

Another embodiment relates to a non-transitory computer-readable medium storing program instructions executable on a computer system of an inspection system for performing a computer-implemented method for wafer inspection. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a wafer inspection system. The system includes an optical subsystem configured to scan a wafer thereby generating image patches in inspection image frames for the wafer. The system also includes one or more computer subsystems coupled to the optical subsystem. The one or more computer subsystems are configured for aligning each of the image patches in each of the inspection image frames to design information for the wafer and detecting defects in the image patches. The computer subsystem(s) are also configured for deriving multiple layer design attributes at locations of the defects from the image patches corresponding to the locations of the detects. In addition, the computer subsystem(s) are configured for building a decision tree with the multiple layer design attributes. The decision tree is used to separate the defects into bins with different yield impacts on a device being formed on the wafer. The computer subsystem(s) are further configured for binning the defects with the decision tree. The water inspection system may be further configured as described herein.

BRIEF DESCRIPTION OF THE DRAWINGS

Other objects and advantages of the invention will become apparent upon reading the following detailed description and upon reference to the accompanying drawings in which.

Figure 1:
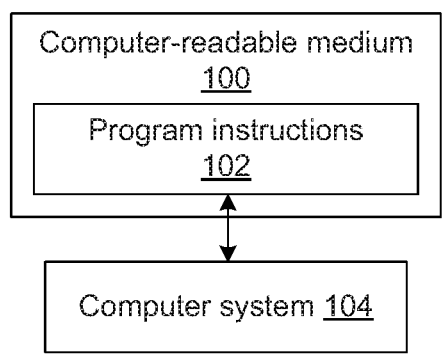
FIG. 1 is a block diagram illustrating one embodiment of a non-transitory computer-readable medium storing program instructions executable on a computer system of an inspection system for performing one or more of the computer-implemented methods described herein.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

The embodiments described herein are configured for design based sampling and binning for yield critical defects. Defect detection that is relevant for yield control is the ultimate goal of in-line inspection. To achieve this goal, inspection recipes tend to focus on maximizing defect of interest (DOI) capture at a reasonable nuisance rate. A "nuisance" or "nuisance defect" is a term commonly used in the art to refer to a potential defect that is detected on a wafer, but that is not an actual defect that is of interest to a user. In this manner, a "nuisance defect" may simply be noise on the wafer that is detected by inspection, which is not representative of any actual defect on the wafer, or an actual defect that the user does not care about.

Binning and sampling from optical inspection are getting more complex due to shrinking design rules and smaller defect sizes. Existing inspection technologies depend on appearance of defects in an optical image. Attributes much as size, detection threshold, intensity, energy, and background are calculated for each detected defect. Decision trees, user defined or canned, are based on calculated attributes to achieve binning and sampling. However, due to limited resolution in optical inspection, the DOIs and nuisance often look alike optically, which makes nuisance filtering, binning, and sampling difficult.

Lately design based inspection and binning (e.g., context based inspection (CBI) and design based binning DBB)) have been effective in filtering nuisance from the non-critical patterns. For example, design based care areas (such as may be used in CBI) and DBB enable inspection and binning on critical patterns to reduce nuisance dramatically.

However, the ability to sample, bin, and monitor defects from yield relevant patterns of interest is critical. In addition, although design based inspection results in significantly reduced nuisance, sampling and binning yield relevant defects from in-line inspection remains a challenge. For example, CBI inspects critical patterns that users are interested in, although the implication of the patterns to yield can be different. DBB is capable of binning defects from multiple layers. However, lack of location accuracy allows using only design attributes such as pattern density.

Yield relevant sampling and binning are extremely critical and needed to produce effective inspection results. As described further herein, it can be achieved by the embodiments described herein with multiple layers of design, prior and/or post to the inspection layer. In addition, the embodiments described herein can be used to separate defects that are the some type of DOIs, but have different yield implications.

One embodiment relates to a method for wafer inspection that includes scanning a wafer with an inspection system thereby generating image patches in inspection image frames for the wafer. The scanning step is performed with an optical subsystem of the inspection system. The optical subsystem and the inspection system may be configured as described further herein. In addition, scanning the wafer may be performed as is described further herein. An "image patch" can be defined as a relatively small portion of an entire inspection image frame generated for the wafer during the scanning. The inspection image frames may be separated into any number of image patches in any arrangement within the image frames. Generally, an "inspection image frame" is a relatively small portion of the entire image generated for the wafer during the scanning that is or can be processed at the same time (e.g., for defect detection) by one or more computer subsystems of the inspection system.

The embodiments described herein are configured for design to optical alignment for each image frame. For example, the method includes aligning each of the image patches in each of the inspection image frames to design information for the wafer. In this manner, the coordinates of locations in the image patches can be determined in design space or in design data coordinates. Aligning the design with the optical patches may be performed in any suitable manner such as by pattern matching. Aligning design with optical patches at every inspection image frame achieves the location accuracy that enables the embodiments described herein. For example, the embodiments described herein require extremely high defect location accuracy for them to be effective. Therefore, the embodiments described herein are also preferably used with inspection systems and methods that produce the best defect location accuracy, which at the moment happens to be CBI performed by the 29xx series of took commercially available from KLA-Tencor, Milpitas, Calif.

In one embodiment, the aligning step includes selecting an alignment site in each of the inspection image frames with both horizontal and vertical features. Identifying and selecting the horizontal and vertical features may be performed using the design data for the wafer and/or images generated for the wafer by the inspection system. "Vertical features" may be any features in the design that can be used to align the image patches in a vertical direction, while "horizontal features" may be any features in the design that can be used to align the image patches in a horizontal direction. The horizontal and vertical directions are the x and y directions in the plane of the wafer. Including vertical and horizontal features in each of the alignment sites increases the accuracy with which the image patches can be aligned to the design.

The aligning step may also include rendering the design and alignment between the rendered design and optical images. For example, in one embodiment, the aligning step includes rendering simulated images from design data for the wafer that illustrate how the design data would appear in the image patches generated for the wafer by the inspection system, and the design information used in the aligning step includes the rendered simulated images. Simulating the images may include simulating how structures in the design data would be formed on the wafer and then simulating how the structures formed on the wafer would appear in images generated by the inspection system. In this manner, the simulating step may be performed based on the parameters and processes involved in the wafer fabrication process as well as the parameters involved in imaging the wafer in the inspection process. Such simulations may be performed in any suitable manner.

The method also includes deriving multiple layer design attributes at the defect locations from the optical patch. For example, the method includes detecting defects in the image patches, which may be performed using any suitable defect detection algorithm(s) and/or method(s) known in the art. In one such example, detecting the defects may include subtracting a reference from the image patches thereby generating difference images and comparing a characteristic of the difference images (e.g., intensity) to a threshold. Characteristics above the threshold may be identified as corresponding to a potential defect while characteristics below the threshold may be identified as not corresponding to a potential defect.

The method also includes deriving multiple layer design attributes at locations of the defects from the image patches corresponding to the locations of the defects. For example, the image patches are aligned to design as described further herein, and the defect locations within the image patches can be determined in the detecting step described above. Therefore, the defect locations can be determined in design data space from the design data space coordinates of the image patches determined in the aligning step. As such, the multiple layer design attributes at the design data space coordinates of the defects can be determined.

As described further herein, the multiple layer design attributes may include design attributes for a layer of the wafer for which the image patches are generated and at least one additional layer of the wafer formed before the layer. In this manner, the design attributes may be determined based on the layer being inspected (or the "current layer" of the wafer) as well as any one or more layers formed under the layer being inspected. In one such example, if the current layer is the metal 2 (M2) layer, the additional layer(s) may include the metal 1 (M1) layer. In another embodiment, the multiple layer design attributes include design attributes for a layer of the wafer for which the image patches are generated and at least one additional layer of the wafer not yet formed on the wafer. In this manner, the design attributes may be determined based on the layer being inspected as well as any one or more layers that will be formed after the layer being inspected has been formed. In the M2 example described above, the additional layer(s) may include the metal 3 (M3) layer. The embodiments described herein may, therefore, use multiple layers of design, prior and/or post current inspection layer, to produce yield relevant sampling and binning.

The multiple layer design attributes can be used to determine a variety of information about the wafer. For example, in one embodiment, the multiple layer design attributes include information for which areas of the wafer are N-type metal-oxide-semiconductor (NMOS) and which areas of the wafer are P-type MOS (PMOS). In another embodiment, the multiple layer design attributes include information for which areas of the wafer are dummy areas and which areas of the wafer are not dummy areas. In an additional embodiment, the multiple layer design attributes include information for which areas of the wafer include dummy structures and which areas of the wafer include device structures. For example, the multiple layer design attributes may indicate if an area of the wafer includes a dummy gate or a device gate. In a further embodiment, the multiple layer design attributes include information for which areas of the wafer include redundant structures and which areas of the wafer include non-redundant structures. For example, the multiple layer design attributes may indicate if an area of the wafer includes a redundant via or a non-redundant via.

The method further includes building a decision tree with the multiple layer design attributes. The decision tree is used to separate the defects into bins with different yield impacts on a device being formed on the wafer. The configuration and format of the decision tree may vary depending on the classification software and/or method that will use the decision tree. One example of suitable classification software is the iDO software that is commercially available from KLA-Tencor. In such an example, the method may include building an iDO tree with multiple layer design attributes to separate the detected events into bins with different yield impacts.

The decision tree is built such that defects that are one type of DOI and have a first of the different yield impacts are separated into a first of the bins and the defects that are the one type of the DOI and have a second of the different yield impacts are separated into a second of the bins. For example, in current binning methods, defects that are located in or near approximately the same geometrical features in the design and that have roughly the same characteristics would be binned together, either as a type of DOI or a type of nuisance. However, defects that are of the same type (meaning the defects themselves have roughly the same characteristics) and are located in the same type of geometry may have different effects on yield based on other characteristics of the design printed on the wafer. These other characteristics may include any of the multiple layer design attributes described herein such as the type of MOS in which they are located, whether they are located in a dummy area, whether they are located in or near a dummy structure, and whether they are located in or near redundant features.

In a first such example, in the case of shallow trench isolation (STI) etch in which planar transistors are formed on a wafer, the embodiments described herein can be used to separate defects that have a greater impact on yield from defects that have a lower impact on yield. In particular, a defect such as an intrusion that is located in the PMOS area of the layer will be more critical than the same defect located in the NMOS area of the layer. The reason for the difference in the criticality is that since electrons travel two times faster than holes, the PMOS area is half the size of the NMOS area. Therefore, the NMOS area can have two contacts for every one contact included in the PMOS area. As such, the NMOS area has better redundancy and therefore is less critical to yield than the PMOS area. In the embodiments described herein, therefore, the defects that are located in PMOS areas can be separated from the defects that are located in NMOS areas thereby separating the defects based on their yield criticality.

In another such example STI etch, two bridging defects having substantially the same characteristics (e.g., size, etc.) may be detected in the same type of structures in a first mask used for the STI etch. However, when the locations of those defects are compared to locations of structures in a post etch mask that will be used to form the next layer on the wafer, one of the defects may be located within device features while the other defect may be located within dummy features. As such, the defects detected on one layer of the wafer may appear to have the same yield criticality when only the design information for that one layer is used to bin the defects. However, when the defects detected on one layer of the wafer are binned based on the defect information from inspection of that one layer in combination with design information from another layer yet to be formed on the wafer, the defects can be separated in a more meaningful manner for yield relevance.

In an additional such example, in the case of gate etching used to form planar transistors, some of the gates included in the layer may be dummy gates while other gates may be active, device gates. Therefore, without considering which gates are dummy gates and which are not, the design information for all gates may appear to be the same and therefore defects that are located on or in any of the gates may be binned together even though they may have dramatically different impacts on yield. However, the embodiments described herein may be used to bin defects based on if they are located on or near a dummy structure thereby separating defects that have no or little yield relevance from defects that have some or great yield relevance.

In another such example, the embodiments described herein may be used for more effective binning of defects detected in a middle of line (MOL) contact layer. For example, some bridging defects may be redundant if they are on the same gate. Therefore, such bridging defects will not even present a timing or reliability issue for devices being fabricated on the wafer. As such, using information about the MOL structure and the locations of defects with respect to that structure can be used to separate defects based on their yield criticalities.

In an additional such example, two defects that have the same characteristics and are located adjacent to vias in the layer of the wafer being inspected may be binned separately in the embodiments described herein if one of the defects is located adjacent to a via that is redundant and if the other of the defects is located adjacent to a via that is not redundant. Therefore, since one of the defects may have an effect on yield (the defect adjacent to the non-redundant via) and the other of the defects will not have an effect on yield (the defect adjacent to the redundant via), the embodiments described herein provide more yield relevant defect information to users of the wafer inspection systems.

In a further such example, some devices may have some back end of line (BEOL) redundancy. In this manner, a metal short may not always be a killer defect because of design redundancy. In other words, in areas that have BEOL redundancy, bridging will not cause a chip to fail. However, bridging defects located in areas that do not have BEOL redundancy may cause the chip to fail. Therefore, separating defects based on whether they are located in areas that have BEOL redundancy or not results in defects being separated into different bins having different yield criticalities.

The method also includes binning the defects with the decision tree. Binning the defects with the decision tree may be performed in any suitable manner. In addition, the information generated by the binning step may be output in any suitable format and may be stored in any of the storage media described herein.

In one embodiment, the decision tree is used to bin defects detected on different wafers on which different devices are being formed. In another embodiment, the decision tree is used to bin defects detected on different wafers for which the scanning step was performed with different optics modes of the inspection system. In an additional embodiment, the decision tree is independent of an optics mode of the inspection system used for the scanning. For example, currently, optical patch based binning and sampling trees are inspection optics mode and layer dependent. With a new device being fabricated on a wafer, the tree often needs to be tweaked to maintain a reasonable result. However, with a tree built from design attributes such as those described herein, it is transferable from device to device and is independent from optics mode selected for inspection. In addition, the multiple layer design attribute based binning and/or classification may be used as a complement to current scanning electron microscope (SEM) classification, which is limited to information from the current layer only.

In another embodiment, the method includes sampling the defects detected on the wafer based on results of the binning step. In this manner, the embodiments described herein can be used for design based yield relevant sampling. The embodiments described herein can be used for sampling for defect discovery (i.e., determining the kinds of defects that are present on the wafer). Sampling the defects from the results of the binning step described herein is advantageous because since different bins correspond to different yield impacts of the defects, the defects that have a greater impact on yield can be sampled more heavily than those that have a lesser impact on yield. In one such example, in the case of STI etch described above, active preferential sampling may be performed based on the results of the binning step such that defects detected in PMOS areas are sampled more heavily than defects detected in NMOS areas. In another such example, in the case of vias described above, defects detected in vias that have no redundancy may be sampled with a higher sampling priority.

One of the main challenges today for the inspection industry is to reduce the time to produce a yield relevant result, which is extremely difficult in defect discovery since the current sampling algorithms are mainly based on optical attributes of the defects without any direct link to yield. The embodiments described herein, however, provide an approach to achieve binning and sampling based on potential yield impact, which is enabled by maximum defect location accuracy through pattern to design alignment within each image frame.

In an additional embodiment, the method includes monitoring the defects detected on the wafer based on results of the binning step. Monitoring the defects may be performed in any manner to determine if the defects being formed on wafers change over some interval of time or wafer. In a further embodiment, the method is performed inline during a fabrication process performed on the wafer. For example, the method may be performed during or after a step of the fabrication process has been performed on the wafer.

In another embodiment, the method includes determining an effect that the defects detected on the wafer have on yield of a fabrication process performed on the wafer based on results of the binning. In the embodiments described herein, the design not only from prior and current layers, but also from future layers may be used to predict the yield impact of defects detected in any inspection process at any stage of the wafer fabrication process. For example, with the use of future layer design information, the potential impact to yield can be obtained without completing all the manufacturing steps on the wafer. In this manner, the embodiments described herein can be used for inline yield estimation.

The aligning, detecting, deriving, building, and binning steps are performed with one or more computer subsystems of the inspection system, which may be configured as described further herein.

Each of the embodiments of the methods described above may include any other step(s) of any other method(s) described herein. Furthermore, each of the embodiments of the methods described above may be performed by any of the systems described herein.

All of the methods described herein may include storing results of one or more steps of the method embodiments in a non-transitory computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. For example, after the method detects the defects, the method may include storing information about the detected defects in a storage medium.

An additional embodiment relates to a non-transitory computer-readable medium storing program instructions executable on a computer system of an inspection system for performing a computer-implemented method for wafer inspection. One such embodiment is shown in FIG. 1. In particular, as shown in FIG. 1, non-transitory computer-readable medium 100 includes program instructions 102 executable on computer system 104. The computer-implemented method includes the steps of the method described above. The computer-implemented method for which the program instructions are executable may include any other step(s) described herein.

Program instructions 102 implementing methods such as those described herein may be stored on computer-readable medium 100. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 2:
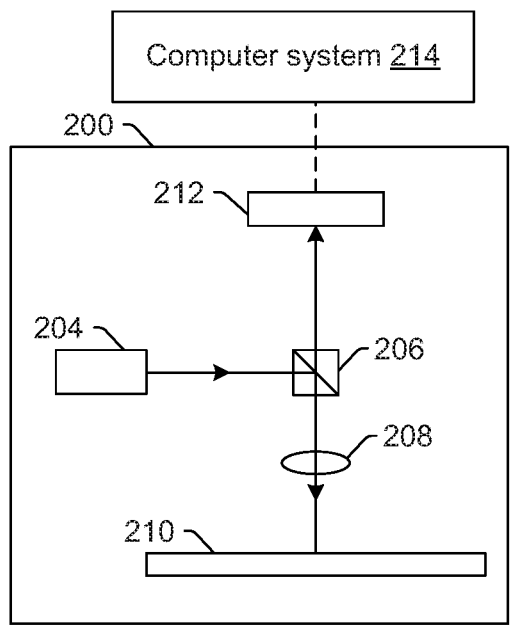
FIG. 2 is a schematic diagram a side view of one embodiment of a wafer inspection system.

Another embodiment relates to a wafer inspection system. One embodiment of such an inspection system is shown in FIG. 2. The wafer inspection system includes on optical subsystem configured to scan a wafer thereby generating image patches in inspection image frames for the wafer. For example, as shown in FIG. 2, the wafer inspection system includes optical subsystem 200.

As shown in FIG. 2, the optical subsystem includes light source 204. Light source 204 may include any suitable light source known in the art such as a laser. Light source 204 is configured to direct light to beam splitter 206, which is configured to reflect the light from light source 204 to refractive optical element 208. Refractive optical element 208 is configured to focus light from beam splitter 206 to wafer 210. Beam splitter 206 may include any suitable beam splitter such as a 50/50 beam splitter. Refractive optical element 208 may include any suitable refractive optical element, and although refractive optical element 208 is shown in FIG. 2 as a single refractive optical element, it may be replaced with one or more refractive optical elements and/or one or more reflective optical elements.

Light source 204, beam splitter 206, and refractive optical element 208 may, therefore, form an illumination channel for the optical subsystem. The illumination channel may include any other suitable elements (not shown in FIG. 2) such as one or more polarizing components and one or more filters such as spectral filters. As shown in FIG. 2, the light source, beam splitter, and refractive optical element are configured such that the light is directed to the wafer at a normal or substantially normal angle of incidence. However, the light may be directed to the wafer at any other suitable angle of incidence.

The optical subsystem may be configured to scan the light over the wafer in any suitable manner.

Light reflected from wafer 210 due to illumination may be collected by refractive optical element 208 and directed through beam splitter 206 to detector 212. Therefore, the refractive optical element, beam splitter, and detector may form a detection channel of the optical subsystem. The detector may include any suitable imaging detector known in the art such as a charge coupled device (CCD). This detection channel may also include one or more additional components (not shown in FIG. 2) such as one or more polarizing components, one or more spatial filters, one or more spectral filters, and the like. Detector 212 is configured to generate output that is responsive to the reflected tight detected by the detector. The output may include signals, signal data, images, image data, and any other suitable output.

As described above, the detector included in the optical subsystem may be configured to detect light reflected from the wafer. Therefore, the detection channel included in the optical subsystem may be configured as a bright field (BF) channel. However, the optical subsystem may include one or more detection channels (not shown) that may be used to detect light scattered from the wafer due to illumination of the wafer. In addition, one or more parameters of the detection channel shown in FIG. 2 may be altered such that the detection channel detects light scattered from the wafer. In this manner, the optical subsystem may be configured as a dark field (DF) tool and/or a BF tool.

The wafer inspection system also includes one or more computer subsystems coupled to the optical subsystem. For example, the computer subsystem(s) may be coupled to a detector of the optical subsystem. In one such example, as shown in FIG. 2, computer system 214 is coupled to detector 212 of optical subsystem 200 (e.g., by one or more transmission media shown by the dashed lines in FIG. 2, which may include any suitable transmission media known in the art). The computer system may be coupled to the detector in any suitable manner. The computer system may be coupled to the optical subsystem in any other suitable manner such that image(s) and any other information for the wafer generated by the optical subsystem can be sent to the computer system and, optionally, such that the computer system can send instructions to the optical subsystem to perform one or more steps described herein.

Computer system 214 is configured for aligning each of the image patches in each of the inspection image frames to design information for the wafer and detecting defects in the image patches. The computer system is also configured for deriving multiple layer design attributes at locations of the defects from the image patches corresponding to the locations of the defects. In addition, the computer system is configured for building a decision tree with the multiple layer design attributes. The decision tree is used to separate the defects into bins with different yield impacts on a device being formed on the wafer. The computer system is further configured for binning the defects with the decision tree. Each of these steps may be performed as described further herein. In addition, the computer system may be configured to perform any other step(s) described herein. The wafer inspection system shown in FIG. 2 may be further configured as described herein.

It is noted that FIG. 2 is provided herein to generally illustrate one configuration of an optical subsystem that may be included in the wafer inspection system embodiments described herein. Obviously, the configuration of the optical subsystem described herein may be altered to optimize the performance of the inspection system as is normally performed when designing a commercial inspection system. In addition, the wafer inspection systems described herein may be implemented using an existing optical subsystem (e.g., by adding functionality described herein to an existing inspection system) such as the 28XX, 29XX, and Puma 9XXX series of tools that are commercially available from KLA-Tencor, Milpitas, Calif. For some such inspection systems, the methods described herein may be provided as optional functionality of the inspection system (e.g., in addition to other functionality of the inspection system). Alternatively, the wafer inspection systems described herein may be designed "from scratch" to provide a completely new inspection system.

Further modifications and alternative embodiments of various aspects of the invention will be apparent to those skilled in the art in view of this description. For example, methods and systems for design based sampling and binning for yield critical defects are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A wafer inspection system, comprising:
    an optical subsystem configured to scan a wafer thereby generating image patches in inspection image frames for the wafer; and
    one or more computer subsystems coupled to the optical subsystem, wherein the one or more computer subsystems are configured for:
        aligning each of the image patches in each of the inspection image frames to design information for the wafer;
        detecting defects in the image patches;
        deriving multiple layer design attributes at locations of the defects from the image patches corresponding to the locations of the defects;
        building a binning method with the multiple layer design attributes, wherein the binning method separates the defects into bins with different yield impacts on a device being formed on the wafer, and wherein the binning method is built such that the defects that are one type of defects of interest and have a first of the different yield impacts are separated into a first of the bins and the defects that are the one type of the defects of interest and have a second of the different yield impacts are separated into a second of the bins; and
        binning the defects with the binning method to thereby separate the defects into the bins with the different yield impacts on the device being formed on the wafer and to separate the one type of the defects of interest having the first of the different yield impacts into the first of the bins and the one type of the defects of interest having the second of the different yield impacts into the second of the bins.

2. The wafer inspection system of claim 1, wherein the multiple layer design attributes comprise design attributes for a layer of the wafer for which the image patches are generated and at least one additional layer of the wafer formed before the layer.

3. The wafer inspection system of claim 1, wherein the multiple layer design attributes comprise design attributes for a layer of the wafer for which the image patches are generated and at least one additional layer of the wafer not yet formed on the wafer.

4. The wafer inspection system of claim 1, wherein said aligning comprises selecting an alignment site in each of the inspection image frames with both horizontal and vertical features.

5. The wafer inspection system of claim 1, wherein said aligning comprises rendering simulated images from design data for the wafer that illustrate how the design data would appear in the image patches generated for the wafer by the optical subsystem, and wherein the design information comprises the rendered simulated images.

6. The wafer inspection system of claim 1, wherein the multiple layer design attributes comprise information for which areas of the wafer are NMOS and which areas of the wafer are PMOS.

7. The wafer inspection system of claim 1, wherein the multiple layer design attributes comprise information for which areas of the wafer are dummy areas and which areas of the wafer are not dummy areas.

8. The wafer inspection system of claim 1, wherein the multiple layer design attributes comprise information for which areas of the wafer comprise dummy structures and which areas of the wafer comprise device structures.

9. The wafer inspection system of claim 1, wherein the multiple layer design attributes comprise information for which areas of the wafer comprise redundant structures and which areas of the wafer comprise non-redundant structures.

10. The wafer inspection system of claim 1, wherein the one or more computer subsystems are further configured for sampling the defects detected on the wafer based on results of the binning.

11. The wafer inspection system of claim 1, wherein the one or more computer subsystems are further configured for monitoring the defects detected on the wafer based on results of the binning.

12. The wafer inspection system of claim 1, wherein the one or more computer subsystems are further configured for performing the aligning, detecting, deriving, building, and binning inline during a fabrication process performed on the wafer.

13. The wafer inspection system of claim 1, wherein the one or more computer subsystems are further configured for binning defects detected on different wafers on which different devices are being formed with the binning method.

14. The wafer inspection system of claim 1, wherein the one or more computer subsystems are further configured for binning defects detected on different wafers scanned with different optics modes of the optical subsystem with the binning method.

15. The wafer inspection system of claim 1, wherein the binning method is independent of an optics mode of the optical subsystem used for scanning the wafer.

16. The wafer inspection system of claim 1, wherein the one or more computer subsystems are further configured for determining an effect that the defects detected on the wafer have on yield of a fabrication process performed on the wafer based on results of the binning.

17. The wafer inspection system of claim 1, wherein the binning method is configured as a decision tree.

18. A method for wafer inspection, comprising:
scanning a wafer with an inspection system thereby generating image patches in inspection image frames for the wafer, wherein the scanning step is performed with an optical subsystem of the inspection system;
aligning each of the image patches in each of the inspection image frames to design information for the wafer;
detecting defects in the image patches;
deriving multiple layer design attributes at locations of the defects from the image patches corresponding to the locations of the defects;
building a binning method with the multiple layer design attributes, wherein the binning method separates the defects into bins with different yield impacts on a device being formed on the wafer, and wherein the binning method is built such that the defects that are one type of defects of interest and have a first of the different yield impacts are separated into a first of the bins and the defects that are the one type of the defects of interest and have a second of the different yield impacts are separated into a second of the bins; and
binning the defects with the binning method to thereby separate the defects into the bins with the different yield impacts on the device being formed on the wafer and to separate the one type of the defects of interest having the first of the different yield impacts into the first of the bins and the one type of the defects of interest having the second of the different yield impacts into the second of the bins, wherein the aligning, detecting, deriving, building, and binning steps are performed with one or more computer subsystems of the inspection system.

19. A non-transitory computer-readable medium, storing program instructions executable on a computer system of an inspection system for performing a computer-implemented method for wafer inspection, wherein the computer-implemented method comprises:
scanning a wafer with an inspection system thereby generating image patches in inspection image frames for the wafer, wherein the scanning step is performed with an optical subsystem of the inspection system;
aligning each of the image patches in each of the inspection image frames to design information for the wafer;
detecting defects in the image patches;
deriving multiple layer design attributes at locations of the defects from the image patches corresponding to the locations of the defects;
building a binning method with the multiple layer design attributes, wherein the binning method separates the defects into bins with different yield impacts on a device being formed on the wafer, and wherein the binning method is built such that the defects that are one type of defects of interest and have a first of the different yield impacts are separated into a first of the bins and the defects that are the one type of the defects of interest and have a second of the different yield impacts are separated into a second of the bins; and
binning the defects with the binning method to thereby separate the defects into the bins with the different yield impacts on the device being formed on the wafer and to separate the one type of the defects of interest having the first of the different yield impacts into the first of the bins and the one type of the defects of interest having the second of the different yield impacts into the second of the bins.

* * * * *